(12) United States Patent
Grimm et al.

(10) Patent No.: US 11,542,464 B2
(45) Date of Patent: Jan. 3, 2023

(54) SINGLE USE PROBE STERILIZABLE BY IRRADIATION AND METHOD FOR THE QUALITY ASSURANCE OF A SINGLE USE PROBE

(71) Applicant: SARTORIUS STEDIM BIOTECH GMBH, Goettingen (DE)

(72) Inventors: Christian Grimm, Heilbad Heiligenstadt (DE); Wei Gao, Kassel (DE); Marco Leupold, Kassel (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 948 days.

(21) Appl. No.: 16/318,604

(22) PCT Filed: Jul. 3, 2017

(86) PCT No.: PCT/EP2017/066513
§ 371 (c)(1),
(2) Date: Jan. 17, 2019

(87) PCT Pub. No.: WO2018/015135
PCT Pub. Date: Jan. 25, 2018

(65) Prior Publication Data
US 2019/0264162 A1   Aug. 29, 2019

(30) Foreign Application Priority Data
Jul. 20, 2016   (DE) .................. 10 2016 113 411.2

(51) Int. Cl.
*G06F 3/06* (2006.01)
*C12M 1/34* (2006.01)
(Continued)

(52) U.S. Cl.
CPC ............ *C12M 41/26* (2013.01); *C12M 41/12* (2013.01); *G06F 3/0604* (2013.01);
(Continued)

(58) Field of Classification Search
None
See application file for complete search history.

(56) References Cited

U.S. PATENT DOCUMENTS 8,963,684 B2 * 2/2015 Nyffeler ................ G11C 11/22
340/5.8
2002/0067265 A1 6/2002 Rudolph
(Continued)

FOREIGN PATENT DOCUMENTS

DE 102014223264 A1 5/2016
WO 2006108500 A1 10/2006

OTHER PUBLICATIONS

PCT International Search Report and Written Opinion dated Oct. 6, 2017 in corresponding Application No. PCT/EP2017/066513, 26 pages.

*Primary Examiner* — Scott C Sun
(74) *Attorney, Agent, or Firm* — Dilworth IP, LLC

(57) ABSTRACT

A single use probe, sterilizable by irradiation, for a single use component for use in a biopharmaceutical process, comprises at least one sensor relevant for the biopharmaceutical process, an RFID tag and a memory rewritable in principle, in which data with respect to an integrity check of the single use probe are stored. A method for quality assurance of such a single use probe comprises: providing the probe with an RFID tag and a memory rewritable in principle, in particular a FeRAM memory as part of the RFID tag; defining a measurement-principle-specific quality parameter of the single use probe; defining a tolerance value for the parameter; performing an integrity check of the probe by first determining and writing into the memory values of the defined quality parameter before sterilization of the probe by irradiation; determining the values of the defined
(Continued)

quality parameter after irradiation; and comparing the values of the quality parameter determined before radiation to those determined after.

16 Claims, 1 Drawing Sheet

(51) Int. Cl.
*G06K 19/07* (2006.01)
*G06Q 50/28* (2012.01)
*G06Q 10/08* (2012.01)

(52) U.S. Cl.
CPC .......... *G06F 3/0655* (2013.01); *G06F 3/0673* (2013.01); *G06K 19/0723* (2013.01); *G06Q 10/0832* (2013.01); *G06Q 50/28* (2013.01)

(56) References Cited

U.S. PATENT DOCUMENTS

| | | |
|---|---|---|
| 2008/0282026 A1 | 11/2008 | Selker et al. |
| 2009/0278493 A1 | 11/2009 | Alden |
| 2010/0060456 A1 | 3/2010 | Forster |
| 2010/0170352 A1 | 7/2010 | Petersen et al. |
| 2015/0266022 A1* | 9/2015 | Eltoukhy .............. B01L 3/5085 506/13 |
| 2015/0310771 A1 | 10/2015 | Atkinson et al. |
| 2015/0323486 A1 | 11/2015 | Schick et al. |

* cited by examiner

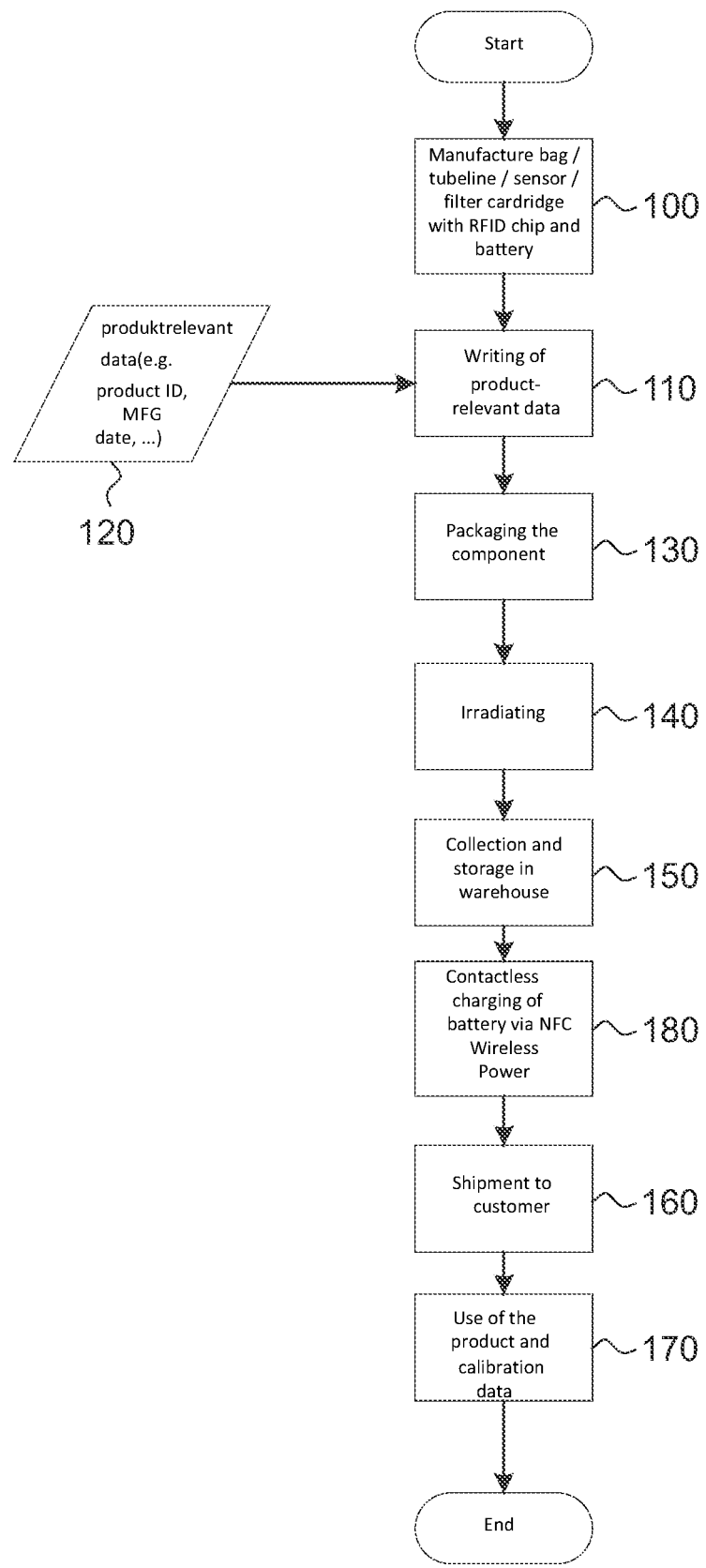

SINGLE USE PROBE STERILIZABLE BY IRRADIATION AND METHOD FOR THE QUALITY ASSURANCE OF A SINGLE USE PROBE

The invention relates to a single use probe which is sterilizable by irradiation. The single use probe is intended for a single use component which is provided for use in a biopharmaceutical process. The invention furthermore relates to a method for the quality assurance of such a single use probe.

BACKGROUND OF THE INVENTION

The trends of recent years in the biopharmaceutical industry increasingly point in the direction of the use of single use components (SU components). The same no longer are used now only in the field of product and process development, but also in the field of clinical trial manufacturing (CTM) for the approval procedure and even in the commercial good manufacturing practice (GMP) in the production of drugs.

In essence, two different approaches for the use of single-use components find their way into the commercial production. On the one hand, especially in new factories, locations or enterprises in particular in Asia, the operators rely on a full single-use approach in which the entire manufacturing chain is covered almost exclusively by single use components. On the other hand, when classical appliances made of stainless steel are present already, the same in general shall also be utilized due to the high purchase price. In this case, so-called hybrid installations comprising existing stainless steel components and newly added single use components are being used. One example is the cultivation of animal cells in a bioreactor.

In particular in the field of the clinical trial manufacturing or even in the surroundings of the method of checking the current quality standards in the field of manufacture (cGMP or Current Good Manufacturing Practice) it is indispensable that the integrity of the reaction vessel is given and thus both a penetration of extraneous organisms and a leakage of the reaction medium from the reactor can be prevented. In the case of stainless steel reactors this is ensured for example by applying a test pressure and determining the pressure drop over time as a measurement parameter, after cleaning, installation and steam sterilization. This pressure test is recorded by the operator of the installation and documented in a suitable way. In single use bioreactors or other systems made of plastics this is effected in a similar way directly before use. Directly after installation of the container, the system is aseptically connected to a pressure testing device via a hose connection. Testing instruments are available by means of which both pressure testing and a cGMP-compliant documentation can be ensured, e.g. the "Sartocheck 4 plus Bag Tester" of Sartorius.

As in contrast to stainless steel systems the single use systems are no fixed installations, the manufacture and the transport of the containers constitute a serious source of possible leakages. To prevent this from happening, a check of the container integrity in part is made already during the production of single use containers. For this purpose, the manufacturer employs systems similar to those being employed by the future user before their use. It is an essential disadvantage of the previous method that the information on the integrity test is not stored on the container itself and therefore must be traced back tediously via the lot number.

In another context a gamma-sterilizable RFID system is known from U.S. Pat. No. 8,963,684 B2, by means of which single-use bioprocess components not manufactured by the original manufacturer can be recognized and thereupon a non-authorized operation can be prevented. For this purpose a FeRAM chip (short for "ferroelectric random access memory chip") is used in order to store error-correctable information on an RFID tag that is attached to a single-use bioprocess component. The information generally is preserved in the memory chip even after the gamma sterilization of the RFID tag and the single-use bioprocess component and can possibly be corrected. There is also described a method for authenticating the single-use bioprocess component, which is meant to reduce the liability risk of the original manufacturer. When a component does not pass an authentication test, a warning is issued to the user or the bioprocess is stopped. In this way, poor-quality counterfeits shall be recognized and users in this case shall be stopped from asserting an unjustified complaint with the original manufacturer.

SUMMARY OF THE INVENTION

It is the object of the invention to especially improve the documentation of the integrity check of a single use sensor unit that is used in a bioprocess and to make it available more easily.

This object is solved by a single use probe comprising the features of the claims and by a method for the quality assurance of a single use probe. Advantageous and expedient embodiments of the single use probe according to the invention and of the method according to the invention are indicated in the respectively associated sub-claims.

The single use probe for a single use component according to the invention, which is provided for use in a biopharmaceutical process, is sterilizable by irradiation and comprises at least one sensor relevant for the biopharmaceutical process, an RFID tag and a memory rewritable in principle, in which data with respect to an integrity check of the single use probe are stored.

The term RFID tag is not to be understood in a limiting sense and shall include all types of transponder units that are operable and/or readable in a wireless or contactless way and all wireless types and standards of transmission, such as NFC (Near Field Communication) etc.

The invention is based on the finding that there are electronic memories that survive the process of a sterilization of the single use probe by irradiation largely unharmed. This opens up the possibility of a dynamic documentation remaining on the product. This means that after a first storage of data in the memory, the information can be changed and/or completed after the radiation sterilization. Thus, the history of a single use probe can be documented carefully and be made available more easily for testing purposes.

The invention thus increases the process safety, as accurate data on the state or the relevant properties of the single use probe are available immediately and on the spot. On the one hand, this leads to fewer complaints with the manufacturer of the single use probe and on the other hand to an improvement of the supply chain.

The memory in which the data are stored before and after a radiation sterilization of the single use probe preferably is part of the RFID tag so that no separate electronic component must be integrated into the single use probe.

A memory suitable for the intended purposes is a FeRAM memory. It was found that this type of memory is largely resistant to the radiation (doses) used in the sterilization of single use components.

Advantageously, product-relevant data also are stored in the memory, in particular a product identification code, a date of manufacture and/or calibration information. These data can relate to the single use probe itself and/or to the single use component for which the single use probe is intended.

Following the idea underlying the invention at least one measurement-principle-specific quality parameter shall be defined depending on the type of probe (e.g. the ohmic resistance for an electronic temperature probe). Before a radiation sterilization of the single use probe, values of this measurement-principle-specific quality parameter shall then be determined—preferably under reproducible conditions—and be stored in the memory.

To provide for a meaningful check of the integrity of the single use probe after its radiation sterilization, values of this measurement-principle-specific quality parameter in turn are determined after the radiation sterilization—preferably under the same conditions—and stored in the memory. Thus, a comparison of the state or the properties of the single use probe is possible before and after the radiation sterilization. If the single use probe no longer satisfies specified quality requirements, it is discarded and not delivered.

In case the single use probe has not become entirely unsuitable due to the radiation sterilization, but only exhibits a comprehensibly shifted or distorted measurement characteristic, which can be compensated by a corresponding calibration, it is not absolutely necessary to refrain from a delivery of the single use probe. In this case, a specification of the single use probe corrected after the radiation sterilization of the single use probe rather can be stored in the memory, which will then be taken into account during the proper use of the single use probe.

In an advantageous embodiment of the memory of the single use probe according to the invention, said memory includes a write protection that after its activation prevents deleting and overwriting of the data stored in the memory.

Advantageously, the memory can also be divided into a free, writable area and a blocked area that no longer is writable. In the blocked area manufacturer data can be stored, which shall not be changed, while information on the integrity check of the single use probe and/or measurement data that will be determined later on during the proper use of the single use probe can be written into the free memory.

It was found that certain types of battery survive the process of a sterilization of the single use probe by irradiation largely unharmed. Based on this surprising finding the RFID tag in an advantageous embodiment is provided with an internal battery. This battery on the one hand can provide the energy required for the proper use of the single use probe. On the other hand, the battery possibly can also support the documentation of the history of the single use probe, which will be discussed below in more detail.

The single use probe for example can be a temperature probe based on the ohmic resistance, whose measurement-principle-specific quality parameter is the ohmic resistance.

Another example for the single use probe is a pH probe based on voltammetry, whose quality parameter specific for the measurement principle is its electric potential in a defined aqueous environment.

The invention also provides an apparatus assembly, comprising a single use probe as defined above, wherein the single use probe includes one or more sensors for detecting certain events and/or ambient conditions, and comprising an accumulator unit to be attached to a packaging outside the single use probe, which in a releasable way is electroconductively connected to an electronic unit of the single use probe or the RFID tag.

The accumulator unit provides for documenting the history of the single use probe over an extended period, in particular in the case of a long storage of the single use probe. As the accumulator unit is rechargeable, it can also serve for the power supply of the sensors of the single use probe after a possible discharge due to the radiation sterilization of the single use probe.

What is preferred particularly is an accumulator unit with a device for wireless charging by an external energy source. In this case, the accumulator unit can be charged in the packed condition of the single use probe, without having to create a cable connection or the like.

Preferably, the accumulator unit is attached to an inner side of an outermost overwrap. The interruption of the releasable electrical connection of the accumulator unit can be recognized and be documented as the time of unpacking and using the single use probe.

The apparatus assembly according to the invention can be completed by a writing device that is configured for the wireless writing of data into the memory of the single use probe, and a reading device that is configured for the wireless reading of data stored in the memory. Of course, the writing device and the reading device can be configured as a combined writing/reading device.

The object of the invention is also solved by a method for the quality assurance of a single use probe that is provided for use in a biopharmaceutical process and includes at least one sensor relevant for the biopharmaceutical process. The quality assurance method according to the invention comprises the following steps:

providing the single use probe with an RFID tag and a memory rewritable in principle, in particular of the type FeRAM, which preferably is part of the RFID tag;

defining a measurement-principle-specific quality parameter of the single use probe;

carrying out a first part of an integrity check of the single use probe before a sterilization of the single use probe by irradiation, wherein current values of the measurement-principle-specific quality parameter are determined and written into the memory;

carrying out a second part of an integrity check of the single use probe after the radiation sterilization, wherein current values of the measurement-principle-specific quality parameter are determined; and evaluating the integrity check, wherein the values of the measurement-principle-specific quality parameter, which are determined before and after the radiation sterilization, are compared with each other.

With respect to the advantages of the method according to the invention reference is made to the corresponding foregoing explanations concerning the single use probe of the invention or the apparatus assembly of the invention.

As already explained with respect to the single use probe according to the invention, the values of the measurement-principle-specific quality parameter of the single use probe, which are determined after the radiation sterilization, can be written into its memory. Thus, the comparative data are available on a long-term basis.

The evaluation of the integrity check preferably is effected on the basis of a previously defined tolerance value that represents a maximum admissible change of the measurement-principle-specific quality parameter. Depending on whether or not this tolerance value is exceeded, corresponding measures can be taken.

The values of the measurement-principle-specific quality parameter preferably are determined by a contactless method before and/or after the radiation sterilization. In any case, the same measurement method should be used in order to obtain comparable results. A contactless determination of measurement values has the advantage that the single use probe can be checked in the packed condition.

The second part of the integrity check can be carried out at any time after the radiation sterilization of the single use probe, i.e. also only shortly or directly before the planned delivery to a customer.

As explained already, information on the performance of the integrity check and/or on storage conditions of the single use probe can be written into the memory in connection with a documentation of the history of the single use probe, as will be described in more detail below.

When the measurement characteristic of the single use probe has changed due to the radiation sterilization, while the basic functionality still is ensured, a corrected specification of the single use probe can be written into the memory after the evaluation of the integrity check. The single use probe then can yet be used properly by taking account of the corrected specification.

When the memory of the single use probe is equipped with a corresponding functionality, a write protection of the memory can be activated before shipment of the single use probe to a customer. Specific manufacturer data thereby remain protected.

The single use probe according to the invention preferably shall be sterilized by irradiation together with a single use component to which the single use probe is attached and/or a packaging of the single use probe or the single use component. The material for the packaging is to be chosen correspondingly. The joint sterilization leads to considerable simplifications in the entire process sequence.

According to a development of the idea underlying the invention the single use probe can record events and/or ambient conditions determined by one or more sensors and write associated data into the memory. The single use probe is supplied with energy via an external accumulator unit as long as the same can provide enough electric power.

Possibly, an internal battery of the RFID tag can take over the energy supply as soon as the energy of the accumulator unit falls below a certain limit value.

As explained already, the accumulator unit shall be configured such that after the radiation sterilization it can be charged again from outside in a contactless way by an external energy source.

According to a further continuation of the idea underlying the invention the electric line between the accumulator unit and the single use probe is interrupted and the time of this event is written into the memory upon opening of a packaging to which the accumulator unit is attached, upon removal of the single use probe from the packaging, or in the case of a defined concussion. This point in time shall document the unpacking and the use or the fact that from this point in time the integrity of the single use probe no longer is ensured on the part of the manufacturer.

BRIEF DESCRIPTION OF THE DRAWINGS

Further features and advantages of the invention can be taken from the following description and from the attached drawing to which reference is made. In the drawing, the only FIGURE by way of example shows the life cycle of a single use probe according to the invention.

DETAILED DESCRIPTION OF THE INVENTION

With reference to the flow diagram shown in the Figure, a typical life cycle of a single use component with a single use probe will be described below, starting with the step 100 of manufacturing the single use component, for example a container (bag) for use in a bioreactor, and the single use probe. The single use probe includes a sensor relevant for a biopharmaceutical process and also is provided with an RFID tag (transponder) that in turn is provided with a memory rewritable in principle, in particular of the type FeRAM.

In a next step 110, product-relevant data 120 are wirelessly written into the memory of the RFID tag by using a suitable writing device. The product-relevant data can comprise a product identification code, the date of manufacture and further details on the single use probe, such as calibration tables etc. The product-relevant data generally can relate to the single use probe and/or to the single use component.

The single use component with the single use probe, possibly together with further SU system components, is packed in step 130 and in step 140 sterilized by irradiation, in particular by gamma irradiation, as a complete unit, i.e. including the packaging. A FeRAM memory in generally survives a sterilization by irradiation, i.e. the data stored in the memory can still be read out after the sterilization process.

In step 150, the sterilized unit is collected (inventorized) and stored, before in step 160 it is shipped to a customer in due course.

The one-time use of the single use component with the single use probe at the customer is represented by step 170.

The outlined life cycle by no means is to be understood in a limiting sense and of course can include further steps.

After the step 140 of irradiating and before the step 160 of shipment to the customer, the integrity of the single use probe can be checked at any time on the part of the manufacturer, as will yet be explained in detail below. In addition, the product-relevant data can be read out from the memory of the RFID tag at any time by means of a suitable reading device and be evaluated in connection with an inventory or quality check or the like. Finally, additional data also can wirelessly be written into the memory of the RFID tag when necessary.

In the following, the performance, documentation and storage of the test or test results of a single use probe integrity check will be described more exactly. The fundamental principle of the check is a comparison of the measurement-principle-specific quality parameters of the respective type of sensor of the single use probe before and after the radiation sterilization. For this purpose, certain sensor-specific quality parameters are selected in advance for the respective type of sensor, which are regarded as suitable for the quality control after the radiation sterilization. In addition, a tolerable change of each sensor-specific quality parameter is defined according to the properties of the respective type of sensor.

In a first part of the integrity check the previously defined measurement-principle-specific quality parameters of the single use probe are determined by a commonly used quality control method before the radiation sterilization. For this purpose, as far as possible, a contactless method is chosen (e.g. optical, electromagnetic-inductive or radioactive). In this case, the quality control can still be carried out when the single use component is packed already. The determined values are written into the memory of the RFID tag of the single use probe.

In a second part of the integrity check the same quality parameters are determined again after the radiation sterilization, preferably again in a contactless way, so that the single use component need not be unpacked. These values then are compared with the values stored in the memory of the RFID chip, which are read out by means of a suitable reading device, and an evaluation is made. If the change of the quality parameters caused by the radiation sterilization lies within the defined tolerance, the quality parameters determined after the radiation sterilization are stored in the memory of the RFID chip as a further data set for monitoring the life cycle. Thereafter, the single use component is cleared for delivery to the customer. In case the change of the quality parameters however lies outside the defined tolerance, the single use component to which the single use probe is attached receives no clearance for delivery.

As mentioned already, the second part of the integrity check can be carried out directly after the radiation sterilization and/or during the storage and/or directly before the planned delivery to a customer.

Furthermore, the date of the performance of the integrity check, of the storage, the storage conditions (place, temperature, etc.) can each be written into the memory of the RFID tag as information. From these data, conclusions as to the current state can be made later on and statements can be made as to whether and possibly how long the single use probe still is suitable for the intended use.

In the following, two concrete examples for the quality assurance of a single use probe will be described.

In the first example, the single use probe shall be a temperature probe based on the ohmic resistance. Hence, the measurement-principle-specific quality parameter here is the ohmic resistance that is to be determined before and after the radiation sterilization at the same ambient temperature as far as possible. For example, before the radiation sterilization a resistance of 107.79 Ohm is measured at a constant temperature of 20° C. and along with the associated measurement conditions written into the memory of the RFID tag.

After the radiation sterilization of the single use component by means of the temperature probe the ohmic resistance of the temperature probe is determined again at the same constant temperature. When the change of the resistance value is greater than a previously defined tolerance value, e.g. +/−0.3 Ohm, the single use component is discarded, as the zero point and the steepness as calibration parameters of the temperature probe have changed so much due to the radiation sterilization that an acceptable temperature measurement at the customer no longer is ensured.

Alternatively, the temperature probe can be subjected to further measurements at other temperatures in order to newly determine the changed zero point and the changed steepness of the single use probe and store it in the memory of the RFID tag. For example, the single use component can be brought to a constant temperature of 5° C. and a constant temperature of 45° C. by means of the temperature probe, and the resistance of the temperature probe at these temperatures can each be measured. The specification of the temperature probe can thereby be corrected and the temperature probe with the corrected specification can be delivered to a customer.

To provide for a contactless measurement of the ohmic resistance, a digital temperature probe can be equipped with a coil for an inductive voltage transmission. From the determinable consumed electric power of the voltage source the ohmic resistance of the temperature probe is inferred.

In the second example, the single use probe shall be a pH probe based on voltammetry. The measurement-principle-specific quality parameter in this case is the electric potential of the pH probe in a defined aqueous environment, which shall be determined before and after the radiation sterilization. For a better understanding it should be noted that the pH probe based on voltammetry must be stored in a potassium chloride solution (KCl) in order to avoid the desiccation of the electrolyte in the probe. In a pH probe, the KCl dissolved in pure water causes an electric potential of 0 mV. On the condition of the storage with such a defined KCl solution, the electric potential therefore can be used as a quality parameter for the pH probe.

For example, before the radiation sterilization an electric potential of the pH probe of 0 mV is measured and along with the associated measurement conditions written into the memory of the RFID tag. After the radiation sterilization of the single use component with the pH probe, the electric potential of the pH probe is again determined under the same measurement conditions. When the change of the electric potential is greater than a previously defined tolerance value, e.g. +/−0.4 mV, the single use component is discarded, as the zero point and the steepness as calibration parameters of the temperature probe have changed so much due to the radiation sterilization that an acceptable measurement of the pH value at the customer no longer is ensured.

Similar to the first example, it is possible in principle under certain conditions to correct the specification of the pH probe with reference to the measurement value determined after the radiation sterilization and possibly further measurement values and to deliver the pH probe with a corrected specification to a customer.

To provide for a contactless measurement of the electric potential, commonly used electromagnetic-inductive methods can be employed.

Before shipment to the customer a write protection of the memory can be activated in the RFID tag in order to protect from manipulations or inadvertent deletion of data that are stored in the memory. It thereby is ensured that the correct data are permanently available.

The customer can read out the product-relevant data and the calibration information when necessary and correspondingly use the same for his purposes.

Optionally, the single use probe can additionally be equipped with a battery arranged in the RFID tag, which at best is partly damaged by irradiation with gamma rays or other rays used for sterilization. The battery in particular serves to supply an electronic unit required for the proper operation of the single use probe with electricity so that the sensor of the single use probe can be used properly and measurement data possibly can be written into the memory when no electricity is available from outside via cables or cableless systems.

In addition, the single use probe can be completed by a rechargeable electric energy source (accumulator). An accumulator unit electroconductively connected to the electronic unit of the single use probe or its RFID tag via a cable or the like is attached for example to the inner side of a carton of an outermost overwrap of the single use component and is provided with a device for wireless charging, such as a suitable near field communication (NFC) antenna. Thus, if necessary, the accumulator unit can be charged in a contactless way by a suitable external energy source.

The use of such an accumulator unit allows to document relevant events and ambient conditions in the history of the single use probe in the memory of the RFID tag over time, in particular before a delivery to a customer. This requires that the single use probe be provided with one or more suitable sensors for detecting the events and/or ambient conditions, such as a temperature sensor, a humidity sensor and/or a radiation sensor.

Upon completion or at a later time before the radiation sterilization the accumulator unit is charged. From this time, the relevant events such as the radiation itself and the radiation dose as well as the ambient temperature and room humidity can be determined in regular or irregular intervals and be written into the memory of the single use probe. These data can be read out in a contactless way at any time by means of a suitable reading device.

Due to the radiation sterilization the accumulator unit can however suffer a partial damage, which leads to a complete or partial discharge. If the energy of the accumulator unit no longer is sufficient for said tasks, this point in time is documented, i.e. written into the memory, and the internal battery of the RFID tag takes over the further power supply.

Owing to the device for wireless charging it is possible in principle, if necessary, to again charge the accumulator in a contactless way from outside by an external energy source after the radiation sterilization, as is shown in the Figure by step 180. Possibly, the frequency of storing and reading out the stored sensor data can also be decreased or adapted in order to ensure the coverage of a desired minimum period of time.

The electrically conductive connection between the RFID tag or the electronic unit of the single use probe and the accumulator unit ideally is designed such that upon opening of the overwrap, upon removal of the content of the overwrap (single use component) or in the case of a defined concussion, the line is interrupted. The internal battery of the RFID tag then takes over the further energy supply. The time of the interruption is documented, i.e. written into the memory, and can be interpreted as an indication that the single use probe is unpacked and utilized or that the integrity of the single use probe no longer is given.

The invention claimed is:

1. An apparatus assembly, comprising:
   a single use probe, sterilizable by irradiation, for a single use component which is provided for use in a biopharmaceutical process, the single use probe comprising at least one sensor relevant for the biopharmaceutical process and/or for detecting certain events or ambient conditions, an RFID tag, and a memory rewritable in principle in which data with respect to an integrity check of the single use probe are stored; and
   an accumulator unit to be attached to a packaging outside the single use probe, which in a releasable way is electro-conductively connected to an electronic unit of the single use probe or to the RFID tag.

2. The apparatus assembly according to claim 1, characterized in that the memory is part of the RFID tag.

3. The apparatus assembly according to claim 1, characterized in that the memory comprises a ferroelectric random access memory chip.

4. The apparatus assembly according to claim 1, characterized in that product-relevant data are stored in the memory.

5. The apparatus assembly according to claim 1, characterized in that values of a measurement-principle-specific quality parameter of the single use probe determined before a radiation sterilization of the single use probe are stored in the memory.

6. The apparatus assembly according to claim 5, characterized in that values of the measurement-principle-specific quality parameter of the single use probe determined after a radiation sterilization of the single use probe are stored in the memory.

7. The apparatus assembly according to claim 6, characterized in that a specification of the single use probe corrected after a radiation sterilization of the single use probe is stored in the memory.

8. The apparatus assembly according to claim 1, characterized by a write protection which after activation prevents a deletion and overwriting of the data stored in the memory.

9. The apparatus assembly according to claim 8, characterized in that the memory includes a free, writable area and a blocked area that no longer is writable.

10. The apparatus assembly according to claim 1, characterized in that the RFID tag is provided with an internal battery.

11. The apparatus assembly according to claim 5, characterized in that it is a temperature probe based on ohmic resistance, whose measurement-principle-specific quality parameter is the ohmic resistance.

12. The apparatus assembly according to claim 5, characterized in that it is a pH probe based on voltammetry, whose measurement-principle-specific quality parameter is its electric potential in a defined aqueous environment.

13. The apparatus assembly according to claim 1, characterized in that the accumulator unit includes a device for wireless charging by an external energy source.

14. The apparatus assembly according to claim 1, characterized in that the accumulator unit is attached to an inner side of an outermost overwrap.

15. The apparatus assembly according to claim 1, comprising a writing device that is configured for wireless writing of data into the memory of the single use probe, and a reading device that is configured for wireless reading out of data stored in the memory.

16. The apparatus assembly according to claim 4, characterized in that the product-relevant data stored in the memory comprises one or more of a product identification code, a date of manufacture or a use-by date.

* * * * *